(12) United States Patent
Turovskiy et al.

(10) Patent No.: US 12,343,527 B2
(45) Date of Patent: Jul. 1, 2025

(54) SYSTEM HAVING ENERGY DELIVERING THERMOCOUPLE ASSEMBLIES

(71) Applicant: Medtronic Ardian Luxembourg S.a.r.l., Luxembourg (LU)

(72) Inventors: Roman Turovskiy, San Francisco, CA (US); Maria Veronica Larios, East Palo Alto, CA (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 646 days.

(21) Appl. No.: 17/546,600

(22) Filed: Dec. 9, 2021

(65) Prior Publication Data

US 2022/0096826 A1   Mar. 31, 2022

Related U.S. Application Data

(60) Continuation of application No. 16/290,565, filed on Mar. 1, 2019, now Pat. No. 11,213,678, which is a
(Continued)

(51) Int. Cl.
*B23P 19/00* (2006.01)
*A61B 18/14* (2006.01)
*A61N 1/28* (2006.01)
*H05K 13/04* (2006.01)
*A61B 18/00* (2006.01)

(52) U.S. Cl.
CPC ............ *A61N 1/28* (2013.01); *A61B 18/1492* (2013.01); *A61B 2018/00404* (2013.01); *A61B 2018/00434* (2013.01); *A61B 2018/00511* (2013.01); *A61B 2018/00577* (2013.01);
(Continued)

(58) Field of Classification Search
CPC .................. A61N 1/28; A61B 18/1492; A61B 2018/00404; A61B 2018/00434; A61B 2018/00511; A61B 2018/00577; A61B 2018/00821; A61B 2018/1435; A61B 2018/144
See application file for complete search history.

(56) References Cited

U.S. PATENT DOCUMENTS

| 6,162,184 A * | 12/2000 | Swanson ............ A61B 18/1492 606/42 |
| 9,066,713 B2 * | 6/2015 | Turovskiy ............... A61B 18/02 |
| 2009/0157066 A1 * | 6/2009 | Satake ................... A61B 18/04 606/27 |

* cited by examiner

*Primary Examiner* — Paul D Kim
(74) *Attorney, Agent, or Firm* — Shumaker & Sieffert, P.A.

(57) ABSTRACT

Systems having energy delivering thermocouple assemblies for achieving neuromodulation by intravascular access are disclosed herein. One aspect of the present technology, for example, is directed to a treatment device having a therapeutic assembly that includes an elongated tubular shaft having a pre-formed spiral shape when in a deployed state (e.g., a radially expanded, generally spiral/helical shape) and a thermocouple assembly helically wrapped about the shaft. In one embodiment, the thermocouple assembly comprises first and second wires composed of dissimilar metals with the first wire including a plurality of exposed and insulated regions along the distal portion of the treatment device. The exposed regions of the first wire define a plurality of energy delivery portions positioned to deliver electrical energy (e.g., RF energy, pulsed energy, etc.) to target tissue adjacent a wall of an artery (e.g., a renal artery) to heat or otherwise electrically modulate neural fibers that contribute to physiological function (e.g., renal function).

21 Claims, 11 Drawing Sheets

Related U.S. Application Data division of application No. 14/021,838, filed on Sep. 9, 2013, now abandoned.

(52) U.S. Cl.
CPC ............ *A61B 2018/00821* (2013.01); *A61B 2018/1435* (2013.01); *A61B 2018/144* (2013.01); *Y10T 29/49002* (2015.01)

SYSTEM HAVING ENERGY DELIVERING THERMOCOUPLE ASSEMBLIES

This application is a continuation of U.S. patent application Ser. No. 16/290,565, filed Mar. 1, 2019, which is a divisional of U.S. patent application Ser. No. 14/021,838, filed Sep. 9, 2013, the entire disclosures of each of which are incorporated herein by reference.

TECHNICAL FIELD

The present technology relates generally to neuromodulation and associated systems and methods. In particular, several embodiments are directed to catheters having energy delivering thermocouple assemblies for intravascular neuromodulation and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine ("NE") spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium (Na+) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radiofrequency ablation) have been shown to reduce blood pressure in patients with treatment-resistant hypertension.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. For ease of reference, throughout this disclosure identical reference numbers may be used to identify identical or at least generally similar or analogous components or features.

DETAILED DESCRIPTION

Figure 1A:
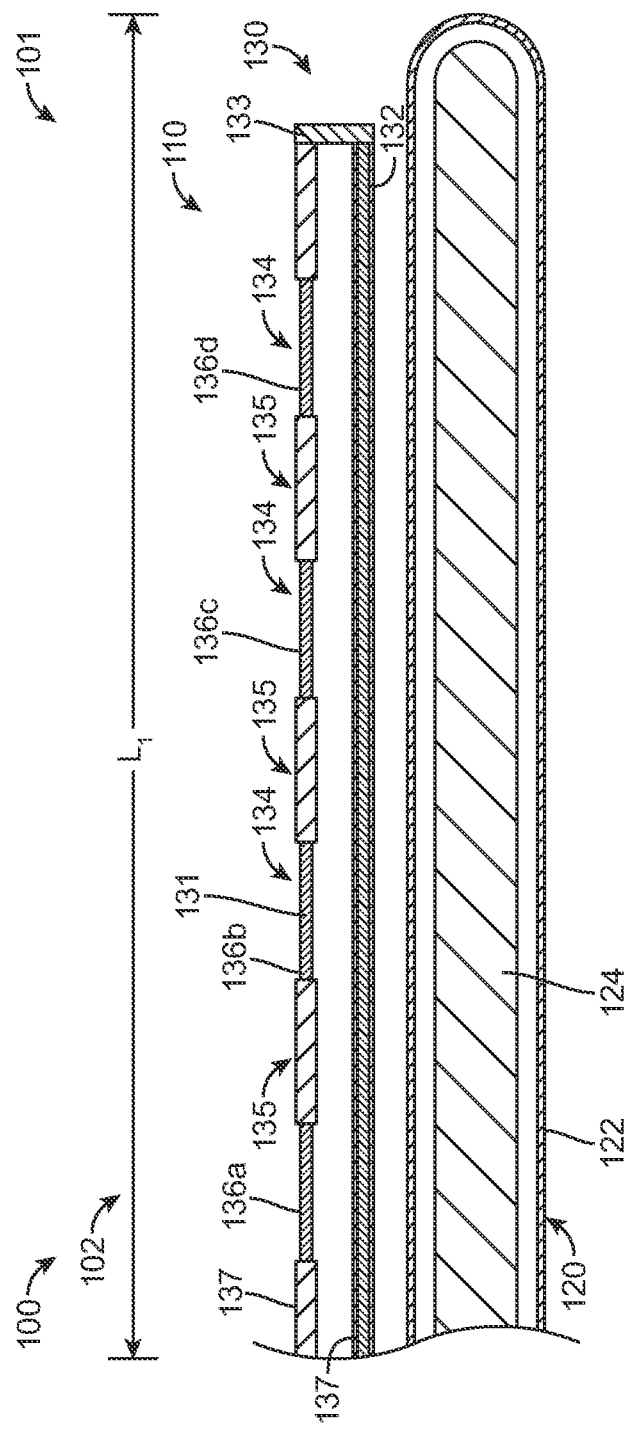
FIG. 1A is an enlarged cross-sectional side view illustrating a therapeutic assembly of a neuromodulation catheter apparatus following a step in a process for assembling the therapeutic assembly from an unassembled state outside a patient in accordance with an embodiment of the present technology.

The present technology is directed to apparatuses, systems, and methods for achieving thermally-induced neuromodulation (i.e., rendering neural fibers that innervate, for example, the kidney or another physiological organ or structure inert or inactive or otherwise completely or partially reduced in function) by percutaneous transluminal intravascular access. In particular, embodiments of the present technology relate to catheters and catheter assemblies having energy delivering thermocouple assemblies and being movable between a delivery or low-profile state (e.g., a generally straight shape) and a deployed state (e.g., a radially expanded shape, generally spiral/helical shape, an expanded lasso shape, J-shape, etc.). The thermocouple assembly may include a plurality of non-insulated energy-delivery portions of a first thermocouple wire (e.g., a silver-coated nickel wire, a silver wire, a nickel wire, a copper wire with biocompatible coating thereon, etc.) that can be coupled to or otherwise extend along or about a longitudinal dimension of a catheter shaft, and may include a second insulated thermocouple wire (e.g., a constantan wire) for thermocouple functionality. The thermocouple assembly is in electrical communication with an energy source or energy generator such that energy is delivered from the non-insulated energy delivery portions of the first thermocouple wire to portions of an artery after being advanced thereto via a catheter along a percutaneous transluminal path (e.g., a femoral artery puncture, an iliac artery and the aorta, a radial artery, or another suitable intravascular path). Any suitable energy modality may be used (e.g., electrical energy such as radiofrequency (RF) energy, pulsed energy, etc.). The catheter or catheter assembly carrying the thermocouple assembly may be sized and shaped so that the non-insulated energy delivery portions contact an interior wall of an artery (e.g., a renal artery, an ovarian artery, testicular artery, external iliac artery, internal iliac artery, internal pudendal artery, uterine artery, celiac artery, superior mesenteric artery, hepatic artery, splenic artery, gastric artery, pancreatic artery, and/or associated arterial branches, etc.) when the catheter is in the deployed state within the artery. The pre-formed expanded shape (e.g., spiral/helical, lasso, J-shape, etc.) of the deployed portion of the catheter carrying the thermocouple assembly allows blood to flow through the helix, which is expected to help avoid occlusion of the artery during activation of the non-insulated energy delivery portions of the thermocouple wire.

Energy-delivery catheter systems for inducing neuromodulation that include separate electrodes or arrays of electrodes can be expensive to manufacture. These designs may require separate wiring of each electrode to a conventional thermocouple wire, as well as complex algorithms and energy generator designs to operate. In contrast, the thermocouple assembly presented herein includes a single energy delivering wire (e.g., the first wire) that can have direct electrical communication with an energy generator, and each non-insulated energy delivery portion of the single wire is in electrical communication with each of the other non-insulated energy delivery portions along the wire. This is expected to reduce manufacturing time and material costs associated with separate electrodes and wiring, as well as reduce the complexity of the control algorithm typically necessary to operate more than one independent electrode or energy delivery element.

Specific details of several embodiments of the technology are described below with reference to FIGS. 1A-5. Although many of the embodiments are described below with respect to devices, systems, and methods for intravascular modulation of sympathetic nerves using thermocouple assemblies, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1A-5.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

Selected Examples of Catheters and Related Devices

Figure 1B:
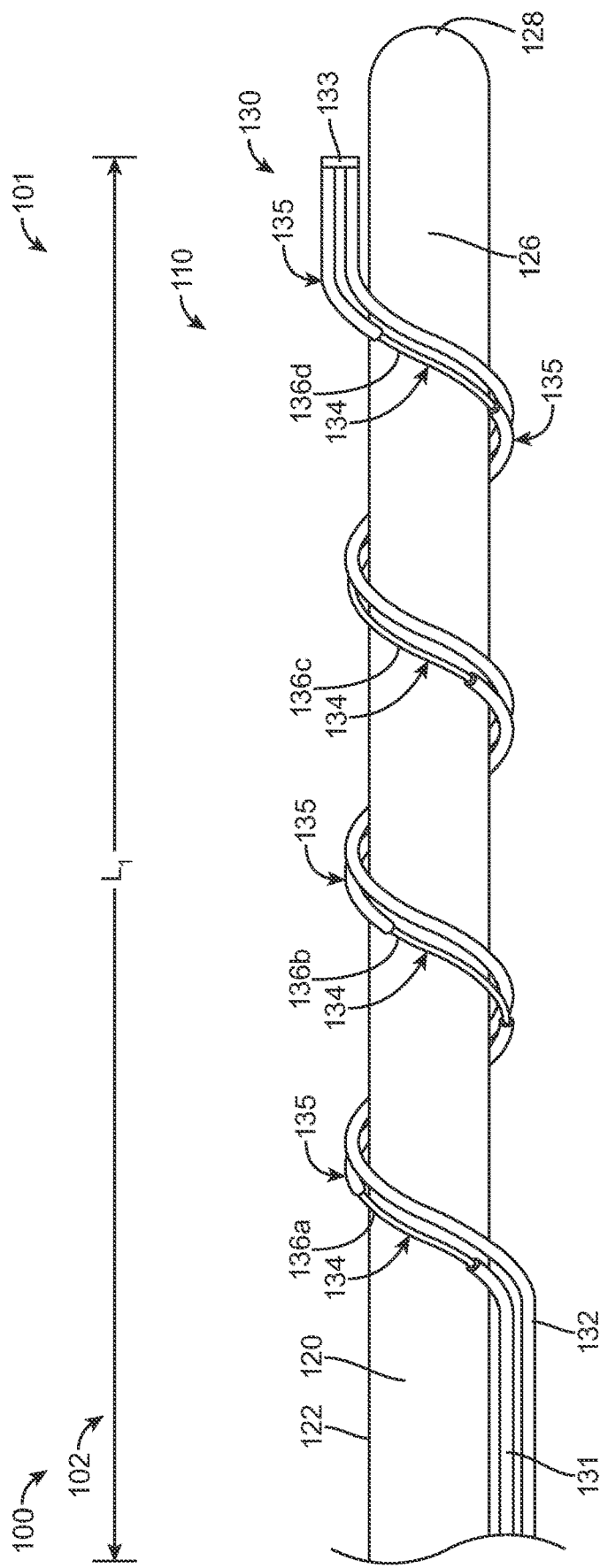
FIG. 1B is a side view of the therapeutic assembly of the catheter apparatus shown in FIG. 1A, following another step in the assembly process of the therapeutic assembly, with the therapeutic assembly shown in a delivery state (e.g., low-profile or collapsed configuration) in accordance with an embodiment of the present technology.
Figure 1C:
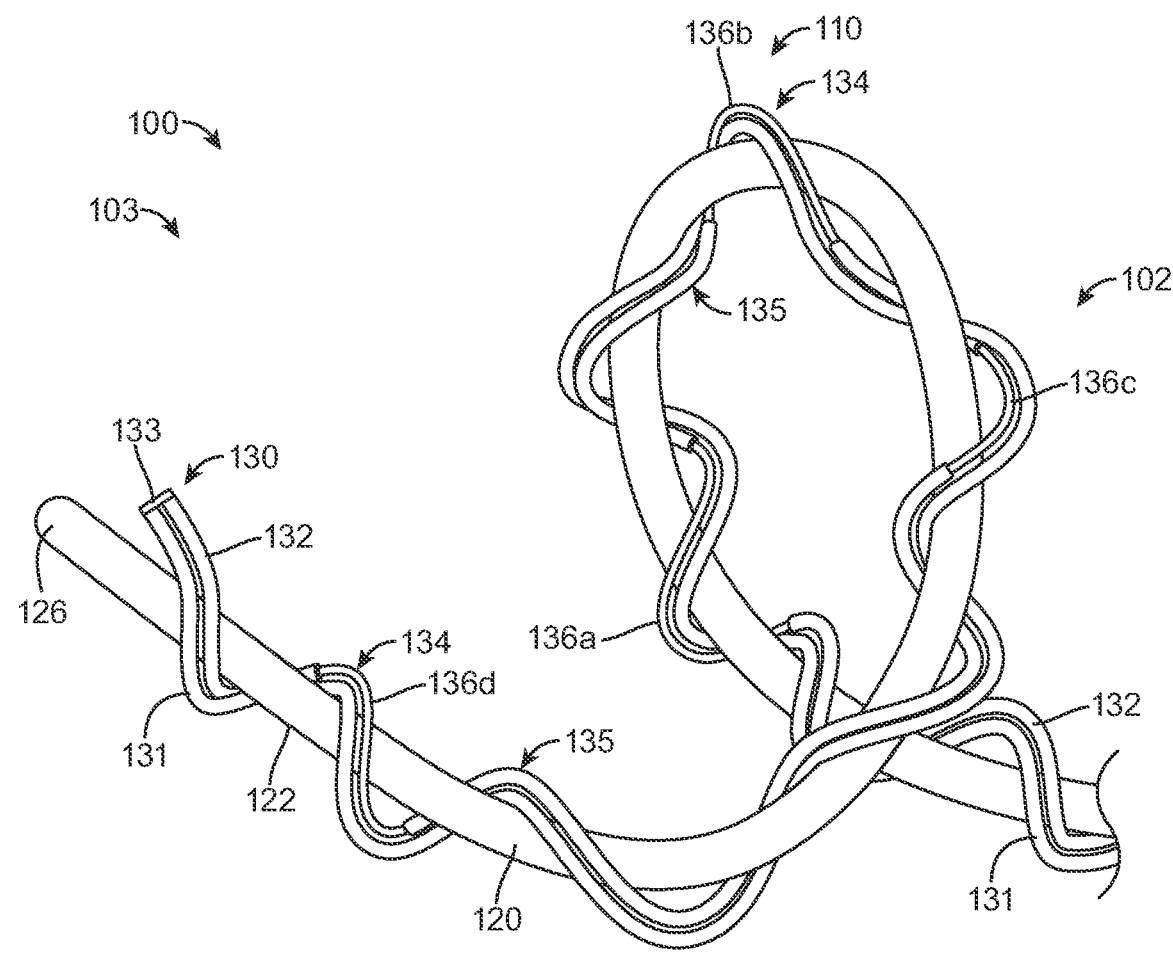
FIG. 1C is a perspective view of the distal portion of the catheter apparatus of FIG. 1B in a deployed state (e.g., expanded configuration) in accordance with an embodiment of the present technology.

FIGS. 1A and 1B illustrate assembly stages following steps in a method of forming a catheter apparatus 100 ("catheter 100") having a therapeutic assembly 110 in a distal portion 102 of the catheter 100 for therapeutically modulating sympathetic nerves in a patient in accordance with an embodiment of the present technology. FIG. 1C is a perspective view of the distal portion 102 of the catheter 100 of FIG. 1B in a deployed state 103 (e.g., expanded configuration). Referring to FIGS. 1A-1C together, the distal portion 102 includes an elongated tubular shaft 120, and the therapeutic assembly 110 can include the shaft 120 and a thermocouple assembly 130 positioned along the shaft 120. The therapeutic assembly 110 can be transformed or actuated between a delivery state 101 (e.g., a low-profile or collapsed configuration, FIG. 1B) and the deployed state 103 (e.g., a radially expanded, generally spiral configuration, FIG. 1C) in which the therapeutic assembly 110 is configured to contact a wall of a blood vessel (e.g., a renal blood vessel).

Referring back to FIGS. 1A and 1B, the therapeutic assembly 110 of the catheter 100 is shown in various stages of assembly for forming the catheter apparatus 100 in a delivery state 101 (e.g., low-profile or collapsed configuration) outside of a patient. As best seen in FIG. 1A, the shaft 120 can include a flexible tube 122 and a pre-shaped spiral/helical control member 124 within the tube 122. The flexible tube 122 may be composed of a polymer material such as: polyamide; polyimide; polyether block amide copolymer sold under the trademark PEBAX; polyethylene terephthalate (PET); polypropylene; aliphatic, polycarbonate-based thermoplastic polyurethane sold under the trademark CARBOTHANE; or a polyether ether ketone (PEEK) polymer that provides the desired flexibility. In other embodiments, however, the tube 122 may be composed of other suitable materials.

As mentioned above, the pre-shaped control member 124 may be used to provide a spiral/helical shape to the shaft 120 in the distal portion 102 of the catheter 100. In one embodiment, the control member 124 can be a tubular structure comprising a nitinol multifilar stranded wire with a lumen therethrough and sold under the trademark HELICAL HOLLOW STRAND (HHS), and commercially available from Fort Wayne Metals of Fort Wayne, Indiana. The tubular control member 124 may be formed from a variety of different types of materials, may be arranged in a single or dual-layer configuration, and may be manufactured with a selected tension, compression, torque and pitch direction. The HHS material, for example, may be cut using a laser, electrical discharge machining (EDM), electrochemical grinding (ECG), or other suitable means to achieve a desired finished component length and geometry.

Forming the control member 124 of Nitinol multifilar stranded wire(s) or other similar materials is expected to provide a desired level of support and rigidity to the therapeutic assembly 110 without additional reinforcement wire(s) or other reinforcement features within the shaft 120. This feature is expected to reduce the number of manufacturing processes required to form the catheter 100 and reduce the number of materials required for the device. In one embodiment, the control member 124 and inner wall of the tube 122 can be in intimate contact with little or no space between the control member 124 and the tube 122. In some embodiments, for example, the tube 122 can have a larger diameter than the control member 124 prior to assembly such that applying hot air to the tube 122 during the manufacturing process shrinks the tube onto the control member 124, as will be understood by those familiar with the ordinary use of shrink tubing materials. This feature is expected to inhibit or eliminate wrinkles or kinks that might occur in the tube 122 as the therapeutic assembly 110 transforms from the relatively straight delivery state 101 to the deployed, generally spiral state 103 (FIG. 1C).

In other embodiments, the control member 124 and/or other components of the shaft 120 (e.g., in the distal portion 102 of the catheter 100) may be composed of different materials and/or have a different arrangement. For example, the control member 124 may be formed from other suitable shape memory materials (e.g., nickel-titanium (Nitinol), wire or tubing besides HHS, shape memory polymers, electro-active polymers) that are pre-formed or pre-shaped into the desired deployed state. Alternatively, the control member 124 may be formed from multiple materials such as a composite of one or more polymers and metals.

FIG. 1A illustrates a stage in the method of forming the therapeutic assembly 110 in the distal portion 102 of the catheter 100 after the thermocouple assembly 130 has been aligned with and positioned alongside the shaft 120. In the embodiment shown in FIG. 1A, the thermocouple assembly 130 includes a conductive first wire 131 and a second wire 132 joined at a junction 133 at least proximate to the shaft 120. The first and second wires 131, 132 can be dissimilar metals. In some embodiments, the first and second wires 131, 132 can be at least partially covered by an insulative cover 137, such as compacted mineral insulation and an outer sheath, or other appropriate conductive wire insulation known in the art. In one embodiment, the conductive first wire 131 can include an insulated energy delivery or transmitting wire that can relay and/or transmit an energy signal from an energy source (not shown), such as an RF energy generator located outside of the patient. In one embodiment, RF signals can be transmitted along a length of the conductive first wire 131 to the therapeutic assembly 110.

FIG. 1A also shows a stage in the method after selected portions of the insulating cover 137 have been removed from along the conductive first wire 131 to form a plurality of exposed regions 134 (e.g., uninsulated regions) separated from each other by insulated regions 135 along a portion of the first wire 131 proximate the shaft 120 (e.g., in the distal portion 102 of the catheter 100). The exposed regions 134 of the conductive first wire 131 can define a plurality of energy delivery portions 136a-136d (referred to collectively as energy delivery portions 136) configured to deliver electrical energy (e.g., RF energy, pulsed energy, etc.) to target tissue. In this embodiment, the energy delivery portions 136 (e.g., the exposed regions 134) are along the same conductive path and, accordingly, commonly connected to an energy source. The thermocouple assembly 130 can include more than one exposed region 134 along the first wire 131. For example the thermocouple assembly 130 can include between 2 and about 8 exposed regions 134 along the first wire 131, or between 2 and about 6 exposed regions 134, or between 2 and about 4 exposed regions 134, or about 4 exposed regions 134. In some embodiments, the energy delivery portions 136a-136d may be equally spaced apart along a length $L_1$ of the therapeutic assembly 110. In other embodiments, however, the number, size and arrangement (e.g., spacing) of the energy delivery portions 136 may vary. For example, a first energy delivery portion 136a may have a first size (e.g., a first length) and a second energy delivery portion 136b may have a second size (e.g., a second length) different than the first size, and/or first and second energy delivery portions 136a and 136b may be spaced apart by a different distance than second and third energy delivery portions 136b and 136c.

The thermocouple assembly 130 can also include the second wire 132, which can be a wire that is at least insulated along the shaft 120. The second wire 132 can run parallel to the first wire 131 and can be electrically coupled to the junction 133. The first wire 131 and the second wire 132 include dissimilar metals such that the electric potential between the two wires 131, 132 formed at the junction 133 relates to a temperature reading at the junction (e.g., at the therapeutic assembly 110). In one embodiment, the first wire 131 comprises a conductive material, such as nickel, silver, or in another embodiment, silver-coated nickel. In some embodiments, the conductive first wire 131 and/or the exposed regions 134 of the first wire 131 can be coated with a biocompatible conductive material (not shown), such as gold or platinum. In some embodiments, a non-biocompatible material (e.g., copper) may be used, for example in a Type T thermocouple or other non-biocompatible thermocouple, along with a biocompatible conductive material such as gold or platinum (e.g., coating for the non-biocompatible materials). Biocompatible materials and/or coatings, however, can be used with any of the thermocouple assemblies 130 described herein. Additional intermediate bonding materials (e.g., tantalum, titanium, etc.) may also be included. In various embodiments, the second wire 132 can be an insulated constantan wire. In a specific embodiment, the thermocouple assembly 130 can be a Type T thermocouple and the first wire 131 can be copper (e.g., gold or platinum coated copper) and the second wire 132 can be constantan. In this example, the thermocouple assembly 130 can measure temperatures in the temperature range of about −200° C. to about 350° C.

FIG. 1B illustrates a stage in the method after the thermocouple assembly 130 has been helically/spirally positioned about the shaft 120 (e.g., in the distal portion 102 of the catheter 100). In this embodiment, the shaft 120 supports the thermocouple assembly 130 about an outer circumference of the distal portion of the catheter 100 and along a length $L_1$ of the therapeutic assembly 110. As shown in FIG. 1B, the thermocouple assembly 130 can be helically positioned (e.g., wound, wrapped, arranged, etc.) about the shaft 120 (e.g., in the distal portion 102 of the catheter 100) while the therapeutic assembly 110 is in the delivery state 101. In one example, the thermocouple assembly 130 can be positioned about the shaft 120 to create a helical shape; however, a variety of helical or non-helical arrangements are suitable for positioning the thermocouple assembly 130 on or about the shaft 120. In some embodiments, the thermocouple assembly 130 may have a pitch of about 1 mm to 12 mm. In other embodiments, however, the thermocouple assembly 130 may have different dimensions.

The thermocouple assembly 130 may be coupled or attached to the shaft 120 (e.g., attached to the flexible tube 122) at one or more locations along the shaft 120 using adhesives (e.g., thermal bonds), fasteners, and/or other suitable attachment mechanisms known in the art (e.g., clips, ties, staples, collars, etc.). In one embodiment, the therapeutic assembly 110 can include proximal and distal connectors or retainers (not shown), such as collars or other suitable fasteners to which proximal and distal portions of the thermocouple assembly 130, respectively, may be attached. In such arrangements, the first and second wires 131, 132 can be helically positioned around the shaft 120 between the proximal and distal connectors (not shown). In various arrangements, such connectors may be attached over select portions of the shaft 120, thereby coupling the thermocouple assembly 130 to the shaft 120. The connectors can be attached to the shaft 120, for example, using thermal bonds, adhesives, interlocking surfaces (e.g., threads), friction fit, snap fit, suction, and/or other suitable attachment mechanisms, or the connectors can be formed integrally with the thermocouple assembly 130 and/or the shaft 120. In other embodiments, the therapeutic assembly 110 does not include additional connectors or attachment means, but can be retained against the shaft 120 with a guide sheath or loading tool (not shown) that is moved over the length $L_1$ of the therapeutic assembly 110 during advancement and retrieval.

The junction 133 of the thermocouple assembly 130 can be positioned at a distal end of the therapeutic assembly 110 which may or may not be a distal end 126 of the shaft 120 (FIGS. 1B and 1C). In one example, the catheter 100 terminates at an atraumatic tip 128 at the distal end 126 of the shaft 120 (FIG. 1B). The atraumatic tip 128 can be a flexible curved tip. In one embodiment, the atraumatic tip 128 may have a distal opening (not shown) for accommodating a guide wire (not shown) that directs the guide wire away from the wall of the artery when the therapeutic assembly 110 is in the pre-set deployed state 103 (FIG. 1C). The curvature of the tip 128 can be varied depending upon the particular sizing/configuration of the therapeutic assembly 110. In some embodiments, the tip 128 may also comprise one or more radiopaque markers (not shown) and/or one or more sensors (not shown). In one embodiment, the tip 128 can be part of (e.g., an extension of or integral with) the shaft 120. In one example, the flexible tip 128 can be a more flexible tapered portion (e.g., about 5 to about 7 mm) of the distal end 126 of the shaft 120. Such an arrangement can be suitable for guidewire delivery of the therapeutic assembly 110 to the target treatment site. In another embodiment, the tip 128 can be a separate component that may be affixed to the distal end 126 of the shaft 120 via adhesive, crimping, over-molding, or other suitable techniques. The tip 128 can be made from a polymer material (e.g., a polyether block amide copolymer sold under the trademark PEBAX, or a thermoplastic polyether urethane material sold under the trademarks ELASTHANE or PELLETHANE), or other suitable materials having the desired properties, including a selected durometer. In other embodiments, the tip 128 may be formed from different material(s) and/or have a different arrangement.

FIG. 1C is a perspective view of the distal portion 102 of the catheter 100 of FIG. 1B in the deployed state 103 (e.g., expanded configuration) in accordance with an embodiment of the present technology. In this embodiment, the control member 124 (FIG. 1A) has a pre-set spiral/helical configuration that defines the deployed state 103 of the therapeutic assembly 110 such that the energy delivery portions 136a-136d of the thermocouple assembly 130 are offset from each other (e.g., both angularly and circumferentially offset relative to a longitudinal axis of the artery and/or angularly offset from each other along an axis of the shaft 120 when the thermocouple assembly 130 is in the deployed configuration). This configuration can provide stable apposition of the energy delivery portions 136a-136d with an inner surface of a wall of the artery (not shown) for treatment. As shown in FIG. 1C, the exposed regions 134 along the first wire 131 of the thermocouple assembly 130 are spaced apart from each other. However, because the insulated regions 134 expose portions of a single first wire 131, the energy delivery portions 136a-136d defined by the exposed regions 134 are in electrical communication with each other (e.g., commonly connected to an energy source).

Once deployed, the therapeutic assembly 110 can deliver neuromodulating energy from a power source (not shown) and through the thermocouple assembly 130 (e.g., through the first wire 131) to the energy delivery portions 136a-136d. The purposeful application of energy (e.g., electrical energy such as RF energy and pulsed energy) to tissue at the treatment location within the artery (e.g., renal artery) can induce one or more desired effects at the treatment location, e.g., broadly across the treatment location or at localized regions of the treatment location. In one embodiment, an RF energy field can be delivered to the target nerves adjacent the wall of the artery via the energy delivery portions 136a-136d. In the illustrated embodiment, the energy delivery portions 136a-136 are spaced apart both circumferentially and longitudinally along the wall of the interior lumen of the artery when the therapeutic assembly 110 is in the deployed state 103. Accordingly, application of energy via the energy delivery portions 136a-136d can result in a plurality of discontinuous lesions along the wall of the interior lumen of the artery. Temperature of the target tissue proximate the therapeutic assembly 110 can be measured and monitored by the thermocouple assembly 130 at the junction 133.

Referring to FIGS. 1B and 1C together, and as described in more detail below with reference to FIG. 5, the catheter 100 may be configured for guidewire based delivery (e.g., over-the-wire ("OTW") delivery, rapid exchange ("RX") delivery) from an access site in which a guide wire (not shown) is initially inserted to a treatment site (e.g., within a renal artery), and the catheter 100 is advanced over the guide wire. For example, the guide wire may be either inserted into or at least partially withdrawn from the shaft 120 (e.g., in the distal portion 102 of the catheter 100) to transform the therapeutic assembly 110 between the delivery state 101 (FIG. 1B) and the deployed state 103 (FIG. 1C). For example, a guide wire (not shown) extending through at least a portion of the length of the catheter 100 (e.g., through a lumen defined by the shaft 120) may be configured to straighten the pre-shaped spiral/helical control member 124 of the catheter 100 during delivery, and the guide wire may be at least partially withdrawn or slideably moved relative to the shaft 120 to allow the therapeutic assembly 110 to transform to the deployed state 103 (FIG. 1C).

Figure 1D:
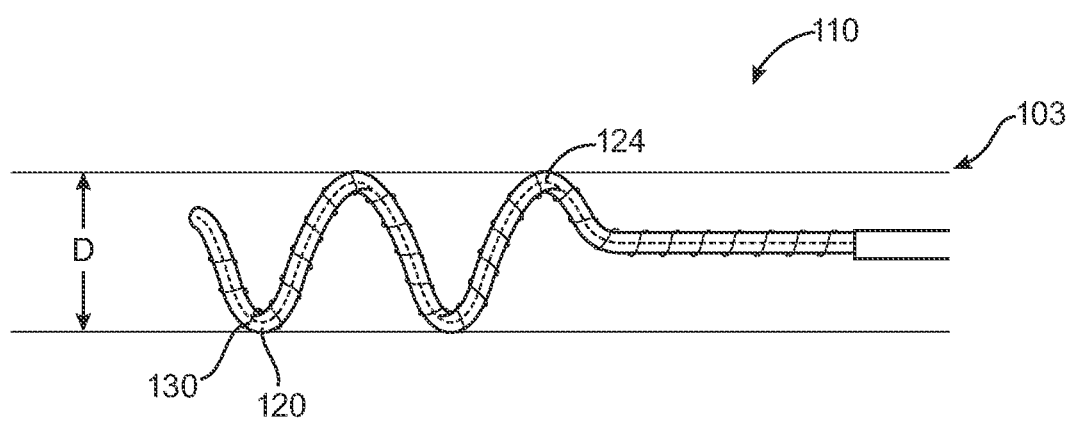
FIG. 1D is a partially schematic side view of the distal portion of the catheter apparatus of FIG. 1C in the deployed state.

As best seen in FIG. 1D, in its deployed state 103, the spiral/helical therapeutic assembly 110 may have an outer diameter D of between about 4 mm and about 9 mm to accommodate, for example, blood vessel sizes having diameters in range of about 3 mm to about 8 mm. As noted above, the control member 124 (shown schematically as a broken line) is itself pre-set into a spiral/helical shape. The dimensions of the spiral/helical shape of the control member 124 may be substantially the same as those of the spiral/helical therapeutic assembly 110.

In the embodiment illustrated in FIGS. 1A-1C, the therapeutic assembly 110 does not include dedicated electrodes separate from the exposed portions 134 of the first wire 131 of the thermocouple assembly 130, or any other conductors or bifilar wires that extend through the lumen or along the surface of the flexible tube 122 or elsewhere along the shaft 120. Instead, the embodiment illustrated in FIGS. 1A-1C is configured to deliver neuromodulating energy to target tissue via the thermocouple assembly 130. An advantage to this embodiment is that the additional manufacturing costs associated with adding separate electrodes and associated wiring of each individual electrode can be avoided while still delivering energy (e.g., RF energy) in suitable frequencies for desirably affecting the target tissue. In other embodiments not shown, however, one or more separate electrodes can be included in the therapeutic assembly 110. For example, a separately wired electrode can be positioned at any location along the length $L_1$ of the therapeutic assembly 110 to deliver the same or a different form of energy as that of the energy delivery portions 136 of the thermocouple assembly 130.

Figure 2A:
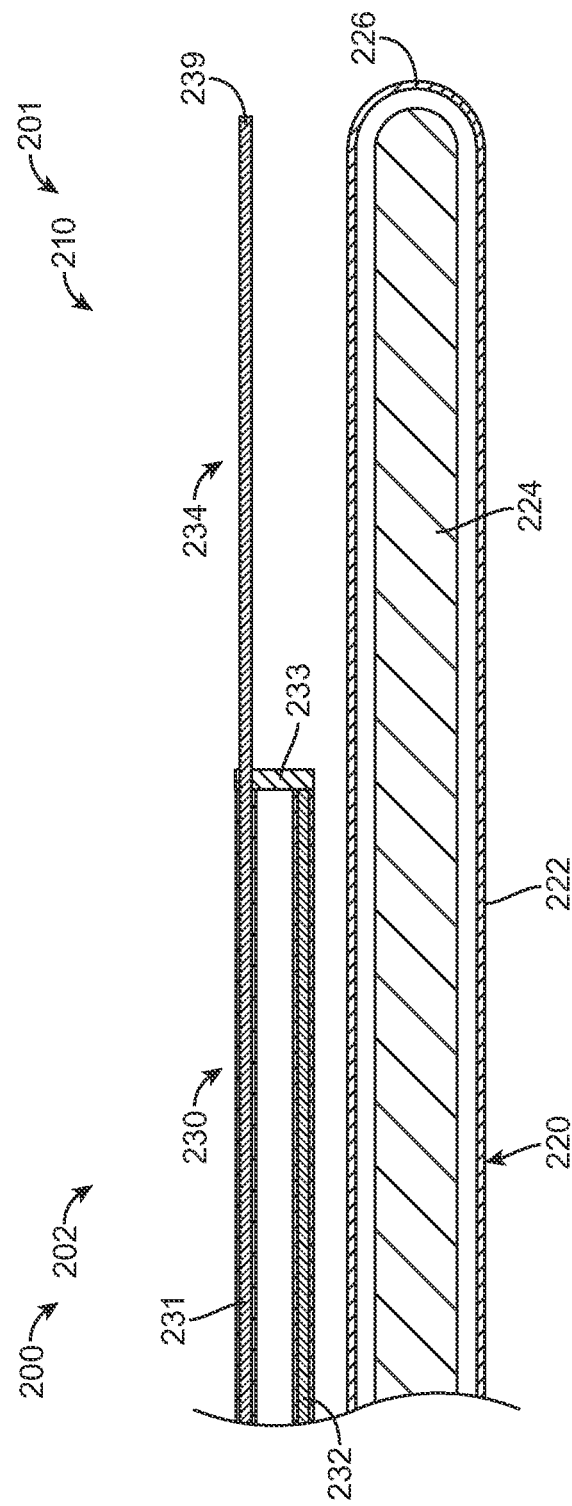
FIG. 2A is an enlarged cross-sectional side view illustrating a therapeutic assembly of a neuromodulation catheter apparatus following a step in a process for assembling the therapeutic assembly from an unassembled state outside a patient in accordance with another embodiment of the present technology.
Figure 2B:
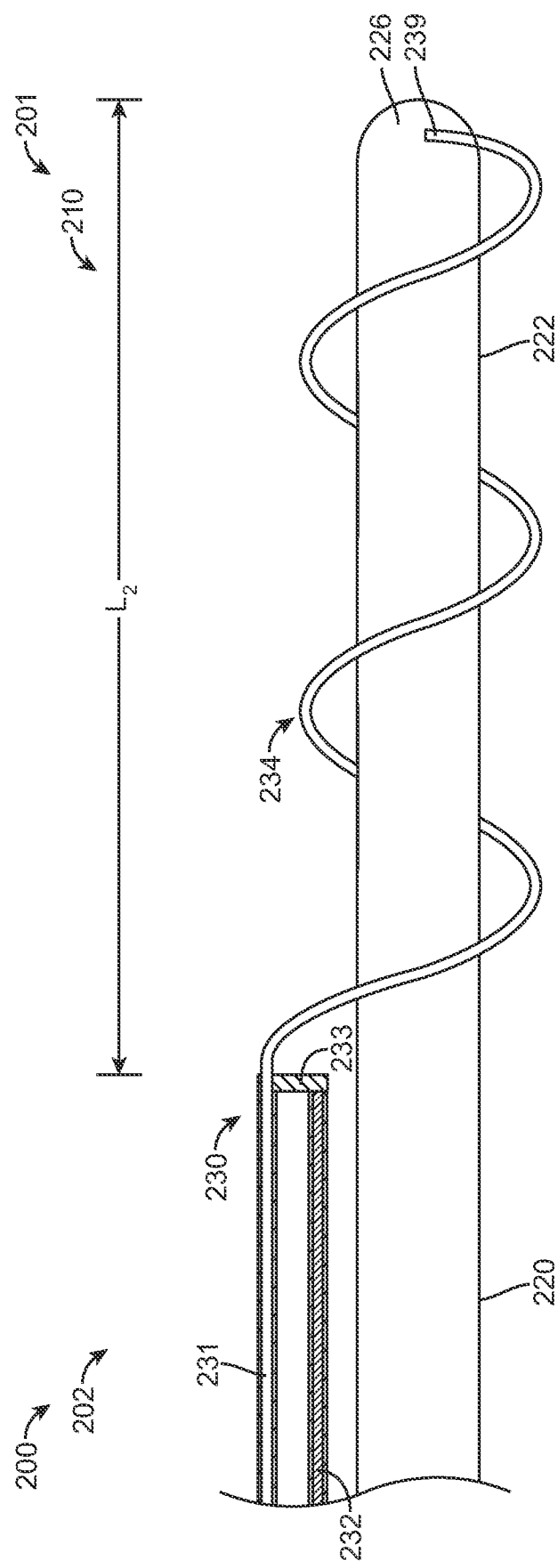
FIGS. 2B and 2C are enlarged, partial cross-sectional side views illustrating assembly stages following additional steps in the process for making the therapeutic assembly of the catheter apparatus shown in FIG. 2A in accordance with embodiments of the present technology.
Figure 2C:
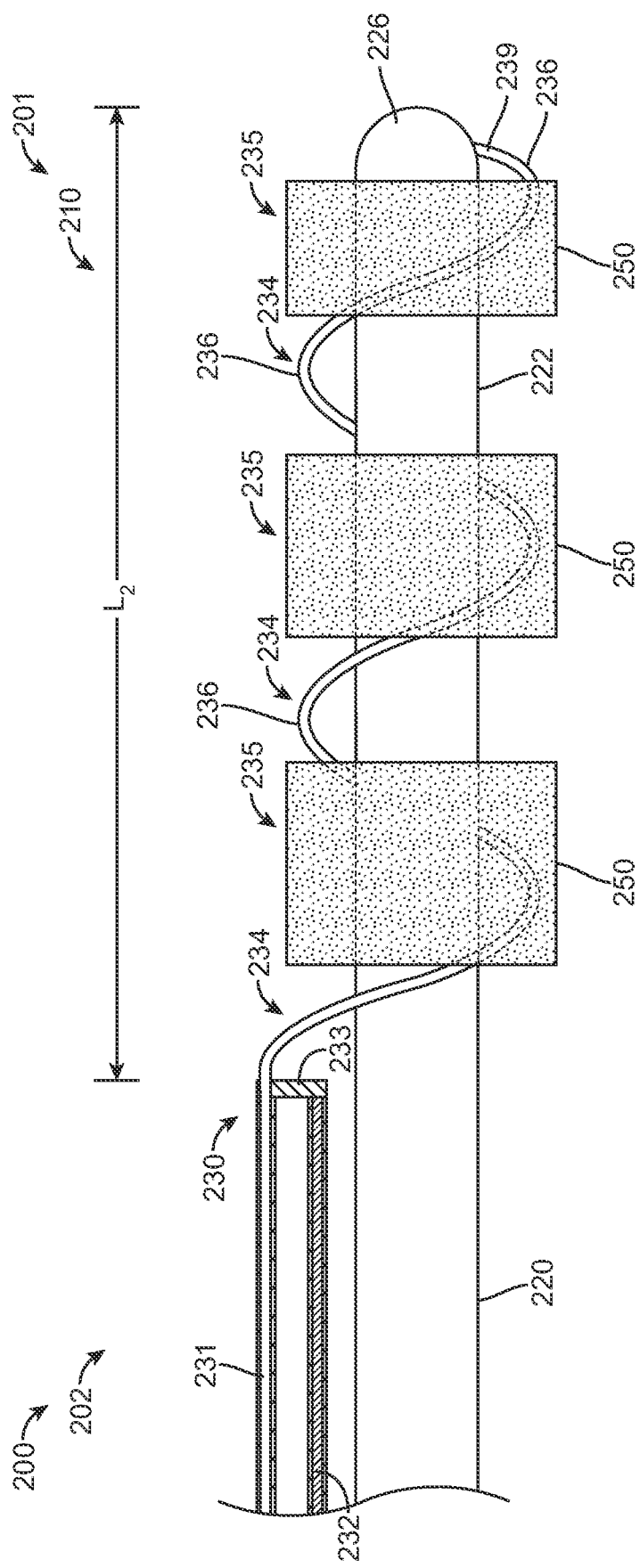
Figure 2D:
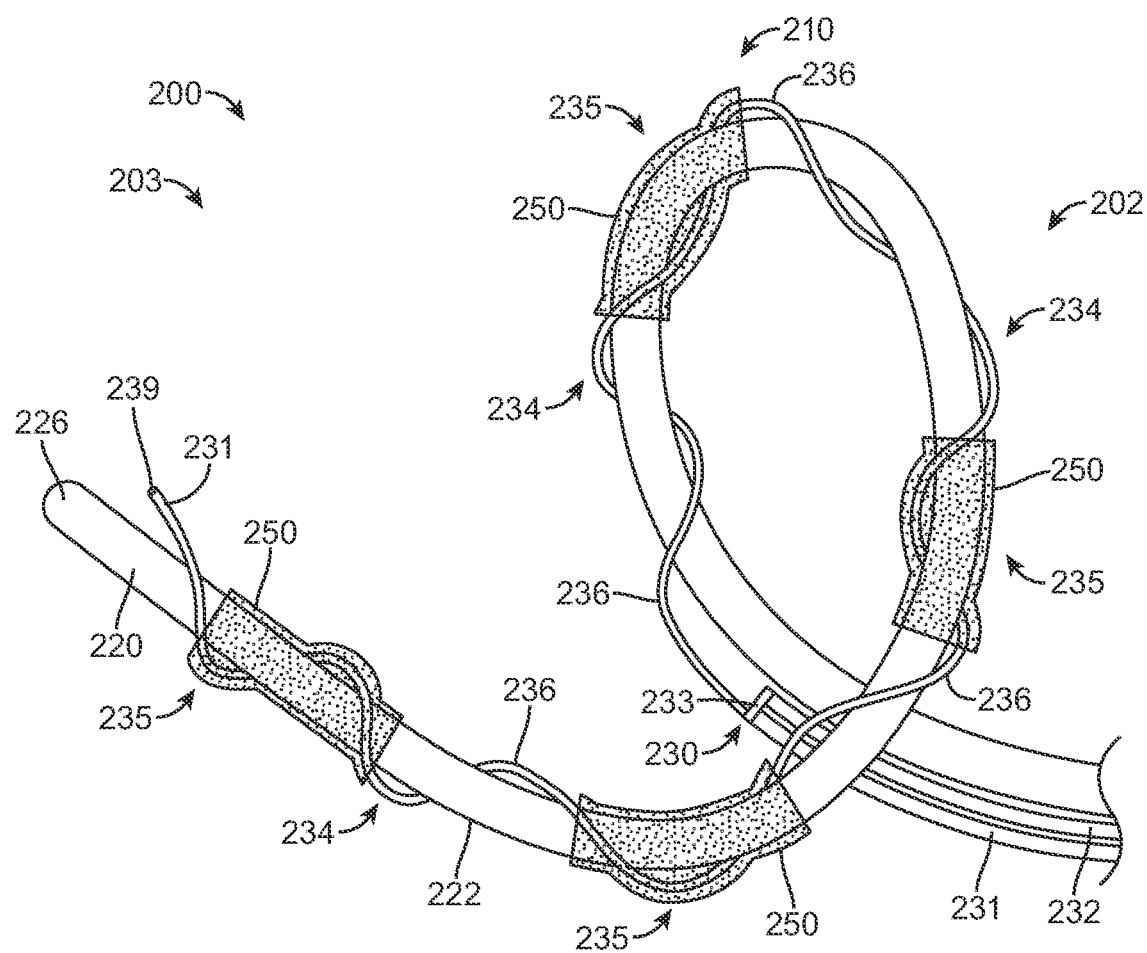
FIG. 2D is a perspective view of the distal portion of the catheter apparatus of FIG. 2C in a deployed state (e.g., expanded configuration) in accordance with an embodiment of the present technology.

FIGS. 2A-2C illustrate assembly stages following steps in a method of forming a catheter apparatus 200 ("catheter 200") having a therapeutic assembly 210 in a distal portion 202 of the catheter 200 for therapeutically modulating sympathetic nerves in accordance with another embodiment of the present technology. FIG. 2D is a perspective view of the distal portion 202 of the catheter 200 of FIG. 2C in a deployed state 203 (e.g., expanded configuration). Referring to FIGS. 2A-2D together, the catheter 200 includes features generally similar to the features of the catheter 100 described above with reference to FIGS. 1A-1C. For example, the distal portion 202 of the catheter 100 includes an elongated tubular shaft 220, and includes a therapeutic assembly 210 having a thermocouple assembly 230 positioned about the shaft 220. However, in the embodiment shown in FIGS. 2A-2D, the thermocouple assembly 230 includes a junction 233 positioned proximal of a distal end 226 of the shaft 220 and includes a single exposed region 234 (e.g., an uninsulated region) of a first wire 231 that extends distal to the junction 233 and toward the distal end 226.

FIG. 2A is an enlarged cross-sectional side view of the therapeutic assembly 210 in a partially assembled state illustrating a stage in the assembly method after the thermocouple assembly 230 has been aligned with and positioned alongside the shaft 220 (e.g., in a distal portion 202 of the catheter 200). Similar to the embodiment described above with respect to FIGS. 1A-1C, the shaft 220 can include a flexible tube 222 and a pre-shaped spiral/helical control member 224 within the tube 222. FIG. 2A also illustrates a step in the process of arranging the thermocouple assembly 230 after an insulating portion has been removed from along the conductive first wire 231 in the region 234 between the junction 233 and an end 239 of the first wire 231. The thermocouple assembly 230 also includes an insulated second wire 232 that terminates at the junction 233.

FIGS. 2B and 2C are enlarged, partial cross-sectional side views illustrating assembly stages following additional steps in the process for arranging the therapeutic assembly 210 of the catheter 200 shown in FIG. 2A. For example, FIG. 2B illustrates a partially assembled stage in the process after the exposed region 234 of the first wire 231 has been helically positioned about the shaft 220. In this embodiment, the shaft 220 supports the exposed region 234 about an outer circumference of the distal portion of the shaft 220 and along a length L2 of the therapeutic assembly 210. As shown in FIG. 2B, the exposed region 234 of the first wire 231 can be helically positioned (e.g., wound, wrapped, arranged, etc.) about the shaft 220 (e.g., in a distal portion 202 of the catheter 200) while the therapeutic assembly 210 is in the delivery state 201. In one example, the thermocouple assembly 230 can be positioned about the shaft 220 to create a helical shape. A variety of helical or non-helical arrangements, however, are suitable for positioning the thermocouple assembly 230 on or about the shaft 220.

FIG. 2C illustrates a final assembly stage in the process after disposing one or more sleeves 250 composed of insulative material about portions of the first wire 231 and the shaft 220 (e.g., in a distal portion 202 of the catheter 200). The catheter 200 is in a delivery state 201 (e.g., low profile or collapsed configuration) in FIG. 2C. The one or more sleeves 250 can be placed along the therapeutic assembly 210 in positions aligned with the exposed region 234 of the first wire 231 to effectively disrupt the exposed region 234. The portions of the first wire 231 that remain exposed (e.g., not covered by the sleeves 250) can define a plurality of energy delivery portions 236, which can deliver or otherwise transmit electrical energy (e.g., RF energy, pulsed energy, etc.) to target tissue in a manner similar to the energy delivery portions 136 described above with respect to FIGS. 1A-1C. In some embodiments, the sleeves 250 may be equally spaced apart along the length L2 of the therapeutic assembly 210 to define the plurality of energy delivery portions 236. In some embodiments, the number of energy delivery portions 236 can be four; however, in other embodiments, the number and arrangement of the energy delivery portions 236 may vary.

In one embodiment, the sleeves 250 can be a flexible and insulative material such as polyethylene terephthalate (PET) heat shrink tubing or other shrink tubing materials known in the art. In other embodiments, the sleeves 250 can be composed of other polymer materials with or without additional insulative layers or materials. For example, the sleeves 250 may comprise one or more of the following materials: polyamide; polyimide; polyether block amide copolymer sold under the trademark PEBAX; polypropylene; aliphatic, polycarbonate-based thermoplastic polyurethane sold under the trademark CARBOTHANE; or a polyether ether ketone (PEEK) polymer that provides the desired material properties. In other embodiments, however, the sleeves 250 may be composed of other or additional suitable materials.

In some embodiments, the sleeves 250 are portions of tubing suitable to place over the distal end 226 of the shaft 220 and positioned at a further proximal site along the therapeutic assembly 210. The sleeves 250 can be heat shrunk around the first wire 231 and the shaft 220 using known processes in the art, such that the exposed region 234 of the first wire 231 (e.g., the portion of the wire 231 after the insulating portion has been removed) is held in place (e.g., helically positioned about the shaft 220) and the sleeves 250 provide intermittently positioned insulated regions 235 along the first wire 231 to define the plurality of energy delivery portions 236. In one embodiment, adhesive (not shown) can be placed between an inner surface of the sleeves 250 and the shaft 220 (e.g., the flexible tube 222) to prevent blood from collecting and/or clotting between the sleeves 250 and the shaft 220. In other embodiments, the sleeves 250 can include material that is wrapped about the shaft 220 and secured into position using known mechanical fastening components or adhesive.

FIG. 2D is a perspective view of the distal portion 202 of the catheter 200 of FIG. 2C in a deployed state 203 (e.g., expanded configuration) in accordance with an embodiment of the present technology. As previously described, the control member 224 (FIG. 2A) has a pre-set spiral/helical configuration that can define the deployed state 203 of the therapeutic assembly 210 such that the energy delivery portions 236 of the thermocouple assembly 230 are offset from each other (e.g., both angularly and circumferentially offset relative to a longitudinal axis of the artery and/or angularly offset from each other along an axis of the shaft 220 when the thermocouple assembly 210 is in the deployed configuration) and may be positioned in stable apposition with an inner surface of a wall of the artery (not shown) for treatment. Additionally, the energy delivery portions 236 along the first wire 231 are defined by the spacing between the sleeves 250 and are spaced apart from each other when the therapeutic assembly 210 is in the deployed state 203. However, the energy delivery portions 236 are commonly connected to each other. Once deployed, the therapeutic assembly 210 (like the therapeutic assembly 110 shown in FIG. 1C) can deliver neuromodulating energy from a power source (not shown) and through the thermocouple assembly 230 (e.g., through the first wire 231) to the target tissue via the energy delivery portions 236.

Figure 3:
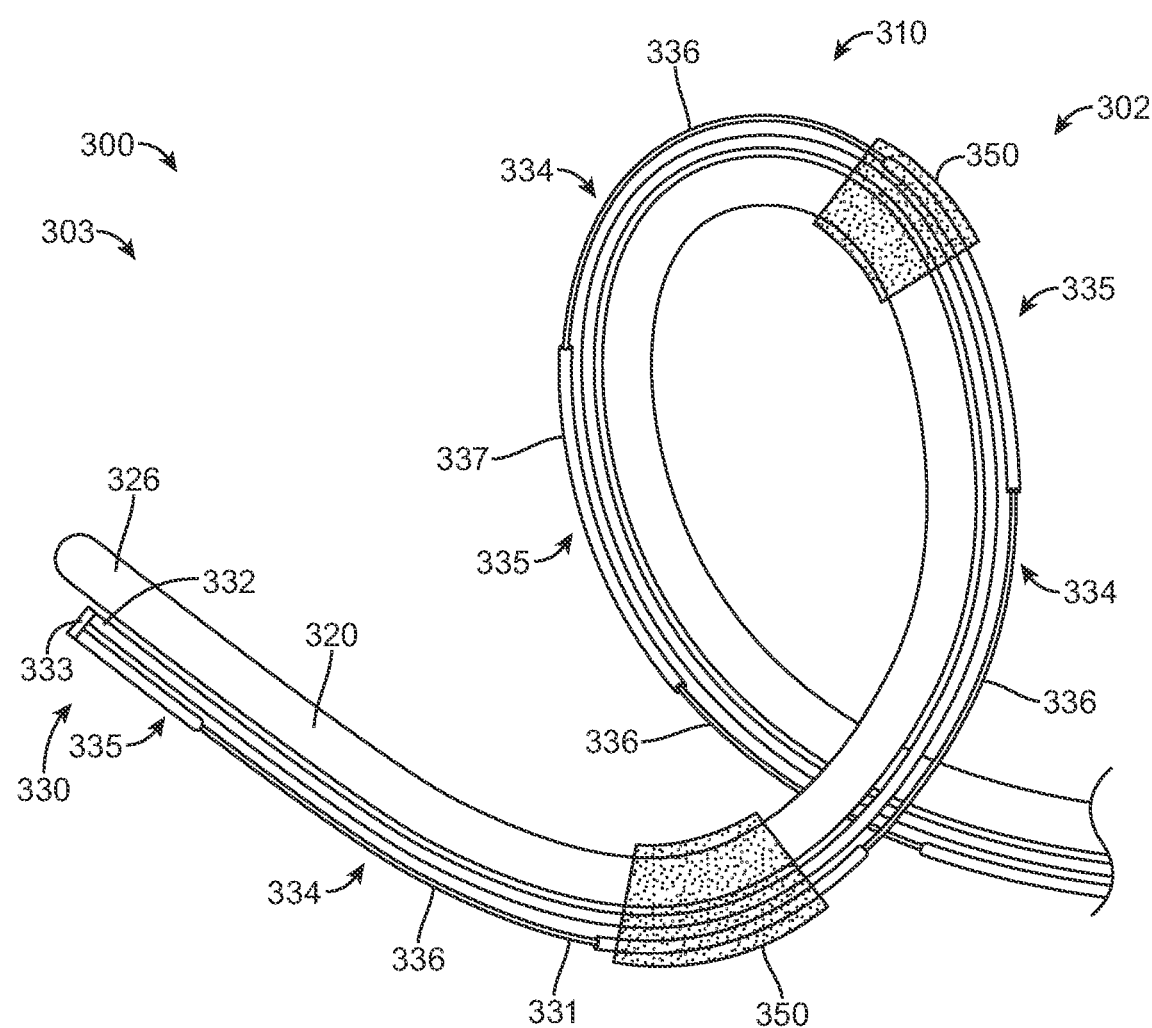
FIG. 3 is a perspective view of a distal portion of a catheter having a therapeutic assembly or treatment section in a deployed state (e.g., expanded configuration) in accordance with a further embodiment of the present technology.

FIG. 3 illustrates a distal portion 302 of a catheter apparatus 300 ("catheter 300") having a therapeutic assembly 310 or treatment section in a deployed state 303 (e.g., expanded configuration) in accordance with a further embodiment of the present technology. FIG. 3 is a perspective view of the distal portion 302 that includes features generally similar to the features of the catheters 100, 200 described above with reference to FIGS. 1A-2D. For example, the distal portion 302 of the catheter 100 includes an elongated tubular shaft 320, and includes the therapeutic assembly 310 having a thermocouple assembly 330 positioned along the shaft 320. However, in the embodiment shown in FIG. 3, the thermocouple assembly 330 is not helically positioned about the shaft 320; rather, the thermocouple assembly 330 is positioned longitudinally along the shaft 320 (e.g., in the distal portion 302 of the shaft 320). The embodiment illustrated in FIG. 3 shows the thermocouple assembly 330 secured to the shaft 320 with one or more sleeves 350, however, one of ordinary skill in the art will recognize that the thermocouple assembly 330 can be secured into position using other known mechanical fastening components (e.g., clips, collars, etc.) or adhesive.

The embodiment illustrated in FIG. 3 includes the thermocouple assembly 330 having an arrangement similar to the thermocouple assembly arrangement shown in FIG. 1A. For example, the thermocouple assembly 330 includes a conductive first wire 331 and a second wire 332 joined at a junction 333 at least proximate to a distal end 326 of the shaft 320. As described above, the first and second wires 331, 332 can be dissimilar metals and can include an insulative cover 337 over the wires, such as compacted mineral insulation and an outer sheath, or other appropriate conductive wire insulation known in the art. The conductive first wire 331 can relay and/or transmit an energy signal from an energy generating source (not shown), such as an RF energy generator located outside of the patient, and along a length of the conductive first wire 331 to the therapeutic assembly 310. Similar to the thermocouple assembly 130 shown in FIG. 1A, the thermocouple assembly 330 includes a plurality of exposed regions 334 (e.g., uninsulated regions) and insulated regions 335 along a portion of the first wire 331 to define a plurality of energy delivery portions 336 at the exposed regions 334. In this embodiment, the energy delivery portions 336 (e.g., the exposed regions 334) are along the same conductive path and, accordingly, commonly connected with each other.

In a pre-deployed configuration of the therapeutic assembly 310, the sleeves 350 can be positioned along the therapeutic assembly 310 to secure the thermocouple assembly 330 to the shaft 320. In this embodiment, the sleeves 350 can be similar to the sleeves 250 described above with respect to FIGS. 2C and 2D, or in another embodiment, the sleeves 350 may not include insulative properties, but serve to couple the thermocouple assembly 330 to the support structure 321. In some embodiments of devices described herein, a sleeve can perform both functions. In a delivery state, the shaft 320 has a longitudinal axis or orientation, and the thermocouple assembly 330 extends at least generally parallel to the longitudinal axis of the shaft 320. When deployed, the therapeutic assembly 310 has a pre-set spiral/helical configuration that defines the deployed state 303 of the therapeutic assembly 310 such that the energy delivery portions 336 of the thermocouple assembly 330 are both longitudinally offset (e.g., along the therapeutic assembly 310) and angularly or circumferentially offset (e.g., as defined by the spiral configuration of the shaft 320) from each other relative to a longitudinal axis of the artery. Accordingly, the energy delivery portions 336 may be positioned in stable apposition with an inner surface of a wall of the artery (not shown) for treatment.

Additional Embodiments

Features of the catheter device components described above and illustrated in FIGS. 1A-3 can be modified to form additional embodiments configured in accordance with the present technology. For example, the catheter 100 illustrated in FIGS. 1A-1C and other catheter apparatuses described above and illustrated in FIG. 2A without sleeves can include sleeves that provide additional coupling of the first and/or second thermocouple wires to the shaft and/or provide additional insulation in selected regions where the sleeves are positioned. Further modifications of the therapeutic assembly 210 illustrated in FIG. 2B can include securing the exposed region 234 of the first wire 231 with non-insulating mechanical components such that a continuous helical lesion (rather than discrete lesions formed in a helical pattern; FIGS. 2C and 2D) can be achieved. Similarly, the catheters described above and illustrated in FIGS. 1A-3 can include one or more control members configured to receive one or more control wires (e.g., pull wires). A control wire can be used, for example, to control (e.g., deflect, angle, position, or steer) a distal portion of the shaft, a thermocouple assembly, or another catheter device component from outside the vasculature.

Features of the catheter device components described above also can be interchanged to form additional embodiments of the present technology. For example, while FIG. 3 illustrates a therapeutic assembly having a non-helically positioned thermocouple assembly arrangement similar to the arrangement shown in FIG. 1A, another embodiment of a catheter in accordance with the present technology could include a therapeutic assembly having a non-helically positioned thermocouple assembly arrangement similar to the arrangement shown in FIG. 2A and including a plurality of insulative sleeves to define energy delivery portions. Additionally, the catheter apparatuses described above can also include additional thermocouple assemblies, electrode elements, wires, and energy delivery features positioned along the distal portion of the shaft.

Selected Examples of Neuromodulation Systems

Figure 4:
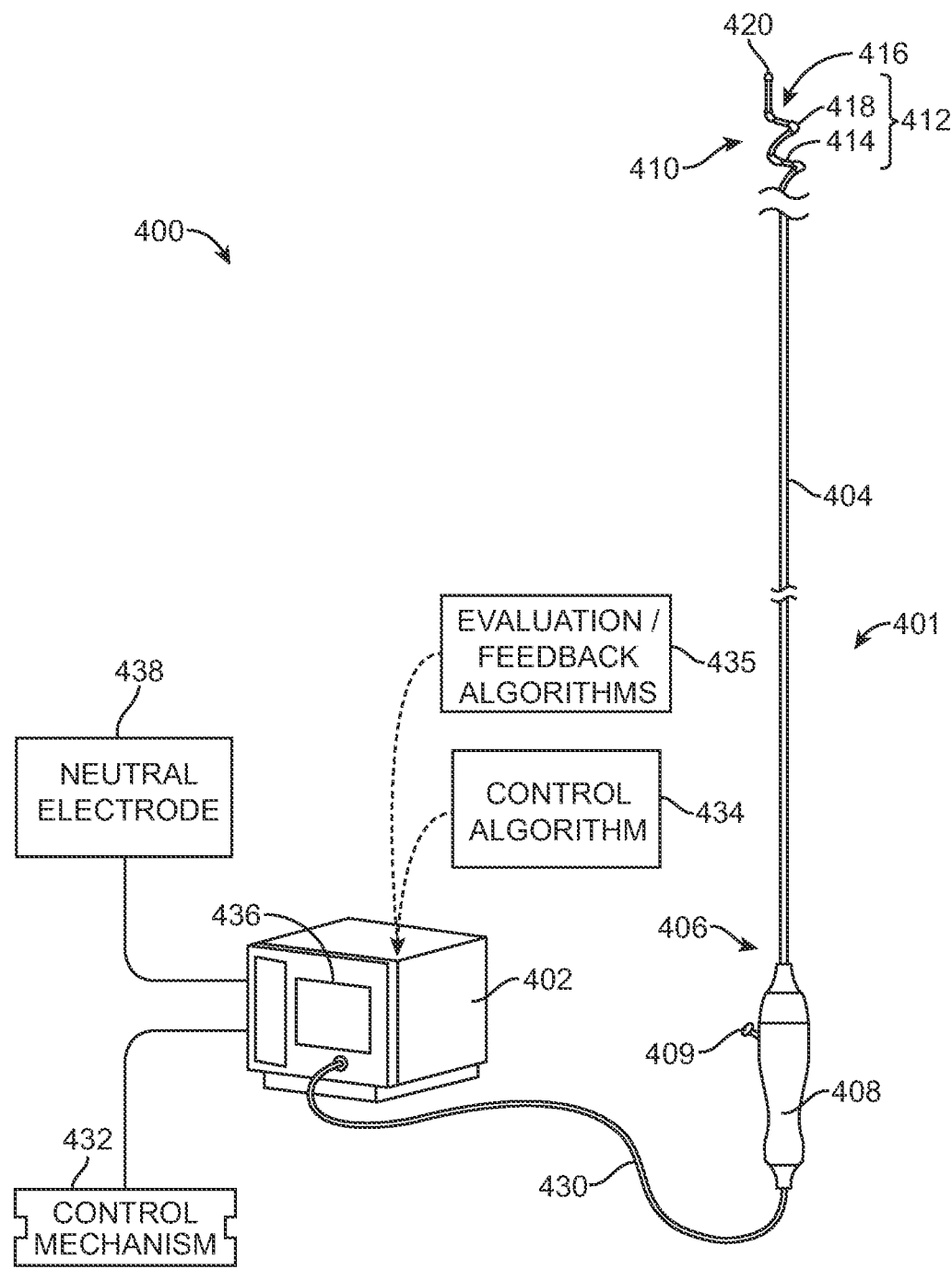
FIG. 4 is a partially schematic diagram of a neuromodulation system configured in accordance with an embodiment of the present technology.

FIG. 4 is a partially schematic illustration of a neuromodulation system 400 ("system 400") configured in accordance with an embodiment of the present technology. The system 400 includes an intravascular catheter 401, which in various embodiments can be any of the catheters 100 (FIGS. 1A-1C), 200 (FIGS. 2A-2D), 300 (FIG. 3), or another of the catheters described above, operably coupled to an energy source or energy generator 402 (e.g., an RF energy generator). The catheter 401 can include an elongated shaft 404 having a proximal portion 406, a handle 408 at a proximal region of the proximal portion 406, and a distal portion 410. The catheter 401 can further include a therapeutic assembly or treatment section 412 (shown schematically) at the distal portion 410 (e.g., attached to the distal portion 410, defining a section of the distal portion 410, etc.). As explained in further detail below, the therapeutic assembly 412 can include a support structure 414 and a thermocouple assembly 416 accompanying the support structure 414. As discussed above with respect to the therapeutic assemblies of the catheter devices illustrated in FIGS. 1A-3, the thermocouple assembly 416 can have an energy delivery wire (e.g., a first wire) having one or more exposed regions that define one or more energy delivery portions 418 along the length of the therapeutic assembly 412 and which is configured to be delivered to a target blood vessel (e.g., an artery, vein or ostium) in a low-profile configuration. As mentioned previously, targeted blood vessels can include, for example, a renal artery, an ovarian artery, testicular artery, external iliac artery, internal iliac artery, internal pudendal artery, uterine artery, celiac artery, superior mesenteric artery, hepatic artery, splenic artery, gastric artery, pancreatic artery, and/or associated arterial branches. One of ordinary skill in the art will recognize that the therapeutic assemblies and catheter devices described herein may be suitable for other blood vessel targets and conditions. Examples of suitable therapeutic and catheter delivery methods for targeting a variety of blood vessels and for therapeutic treatment of a variety of conditions are described, for example, in U.S. patent application Ser. No. 13/691,594 filed Nov. 30, 2012; U.S. patent application Ser. No. 13/691,556 filed Nov. 30, 2012; International Publication No. PCT/US2013/029690, filed Mar. 7, 2013; International Publication No. PCT/US2013/029547, filed Mar. 7, 2013; International Publication No. PCT/US2013/029679, filed Mar. 7, 2013; and International Publication No. PCT/US2013/029574, filed Mar. 7, 2013 each of which are incorporated herein by reference in their entireties.

Upon delivery to the target treatment site within the target blood vessel (e.g., renal blood vessel), the therapeutic assembly 412 is further configured to be deployed into an expanded state (e.g., a generally spiral/helical configuration, an expanded lasso or J-shaped configuration, etc.) for delivering energy at the treatment site and providing therapeutically-effective thermally-induced neuromodulation. Alternatively, the deployed state may be non-spiral provided that the deployed state provides adequate contact between energy delivery portions and the inner surface of the vessel wall. The therapeutic assembly 412 may be transformed between the delivery and deployed states using a variety of suitable mechanisms or techniques (e.g., self-expansion, remote actuation via an actuator, etc.). In a specific example, the neuromodulation assembly 412 may be placed or transformed into the deployed state or arrangement via remote actuation, e.g., via an actuator 409, such as a knob, pin, or lever carried by the handle 408. In another example, following placement of the therapeutic assembly at the treatment site, advancement of a pre-shaped or expandable element or wire (e.g., a Nitinol wire) into a lumen of the shaft or flexible tube can cause the therapeutic assembly to assume its deployed state.

The proximal end of the therapeutic assembly 412 is carried by or affixed to the distal portion 410 of the elongated shaft 404. A distal end of the therapeutic assembly 412 may terminate the catheter 401 with, for example, an atraumatic tip 420. In some embodiments, the distal end of the therapeutic assembly 412 may also be configured to engage another element of the system 400 or catheter 401. For example, the distal end of the therapeutic assembly 412 may define a passageway for receiving a guide wire (not shown) for delivery of the treatment device using OTW or rapid exchange ("RX") techniques. Further details regarding such arrangements are described below.

The catheter 401 can be electrically coupled to the energy source 402 via a cable 430, and the energy source 402 (e.g., an RF energy generator) can be configured to produce a selected modality and magnitude of energy for delivery to the treatment site via the thermocouple assembly's energy delivery portions 418 along the first wire. As described in greater detail below, thermocouple wires (not shown) can extend along the elongated shaft 404 or through a lumen in the shaft 404 to the therapeutic assembly 412 at the distal portion 410 of the elongated shaft 404 and transmit the treatment energy to the energy delivery portions 418 (e.g., the exposed regions of the energy delivering thermocouple wire). Accordingly, each energy delivery portion 418 can receive and deliver energy supplied by the single energy delivery wire within the thermocouple assembly 416 instead of each portion 418 having its own supply wire. The energy delivery portions 418 are positioned along the same electrical power wire or line, and accordingly, deliver power in a simultaneous fashion.

A control mechanism 432, such as a foot pedal or handheld remote control device, may be connected to the energy source 402 to allow the clinician to initiate, terminate and, optionally, adjust various operational characteristics of the energy source 402, including, but not limited to, power delivery. The remote control device (not shown) can be positioned in a sterile field and operably coupled to the thermocouple assembly, and specifically to the energy delivering thermocouple wire having the exposed (e.g., uninsulated) energy delivery portions 418, and can be configured to allow the clinician to activate and deactivate the energy delivery to the energy delivery portions 418. In other embodiments, the remote control device may be built into the handle assembly 408.

The energy source or energy generator 402 can be configured to deliver the treatment energy via an automated control algorithm 434 and/or under the control of a clinician. For example, the energy source 402 can include computing devices (e.g., personal computers, server computers, tablets, etc.) having processing circuitry (e.g., a microprocessor) that is configured to execute stored instructions relating to the control algorithm 434. In addition, the processing circuitry may be configured to execute one or more evaluation/feedback algorithms 435, which can be communicated to the clinician. For example, the energy source 402 can include a monitor or display 436 and/or associated features that are configured to provide visual, audio, or other indications of power levels, sensor data, and/or other feedback. The energy source 402 can also be configured to communicate the feedback and other information to another device, such as a monitor in a catheterization laboratory.

In some embodiments, the system 400 may be configured to provide delivery of a monopolar electric field via the energy delivery portions 418. In such embodiments, a neutral or dispersive electrode 438 may be electrically connected to the energy generator 402 and attached to the exterior of the patient (as shown in FIG. 5). The individual energy delivery portions (e.g., energy delivery portions 136, 236 and 336 from FIGS. 1A-3) are connected to the energy generator 402 and are sized and configured to contact an internal wall of the artery (e.g., the renal artery). In the illustrated embodiment, the energy delivery portions may be operated in a monopolar or unipolar mode. In this arrangement, a return path for the applied RF electric field is established, e.g., by the external dispersive electrode 438, also called an indifferent electrode or neutral electrode. The monopolar application of RF electric field energy serves to ohmically or resistively heat tissue in the vicinity of the electrode. The application of the RF electrical field thermally injures tissue. The treatment objective is to thermally induce neuromodulation (e.g., necrosis, thermal alteration or ablation) in the targeted neural fibers. The thermal injury forms a lesion in the vessel wall. Alternatively, an RF electrical field may be delivered with an oscillating or pulsed intensity that does not thermally injure the tissue whereby neuromodulation in the targeted nerves is accomplished by electrical modification of the nerve signals.

The system 400 can also include one or more additional sensors (not shown) located proximate to or within the energy delivery portions 418. For example, the system 400 can include one or more other temperature sensors (e.g., one or more additional thermocouples, thermistors, etc.), impedance sensors, pressure sensors, optical sensors, flow sensors, and/or other suitable sensors connected to one or more supply wires (not shown) that transmit signals from the sensors and/or convey energy to the therapeutic assembly 412.

Figure 5:
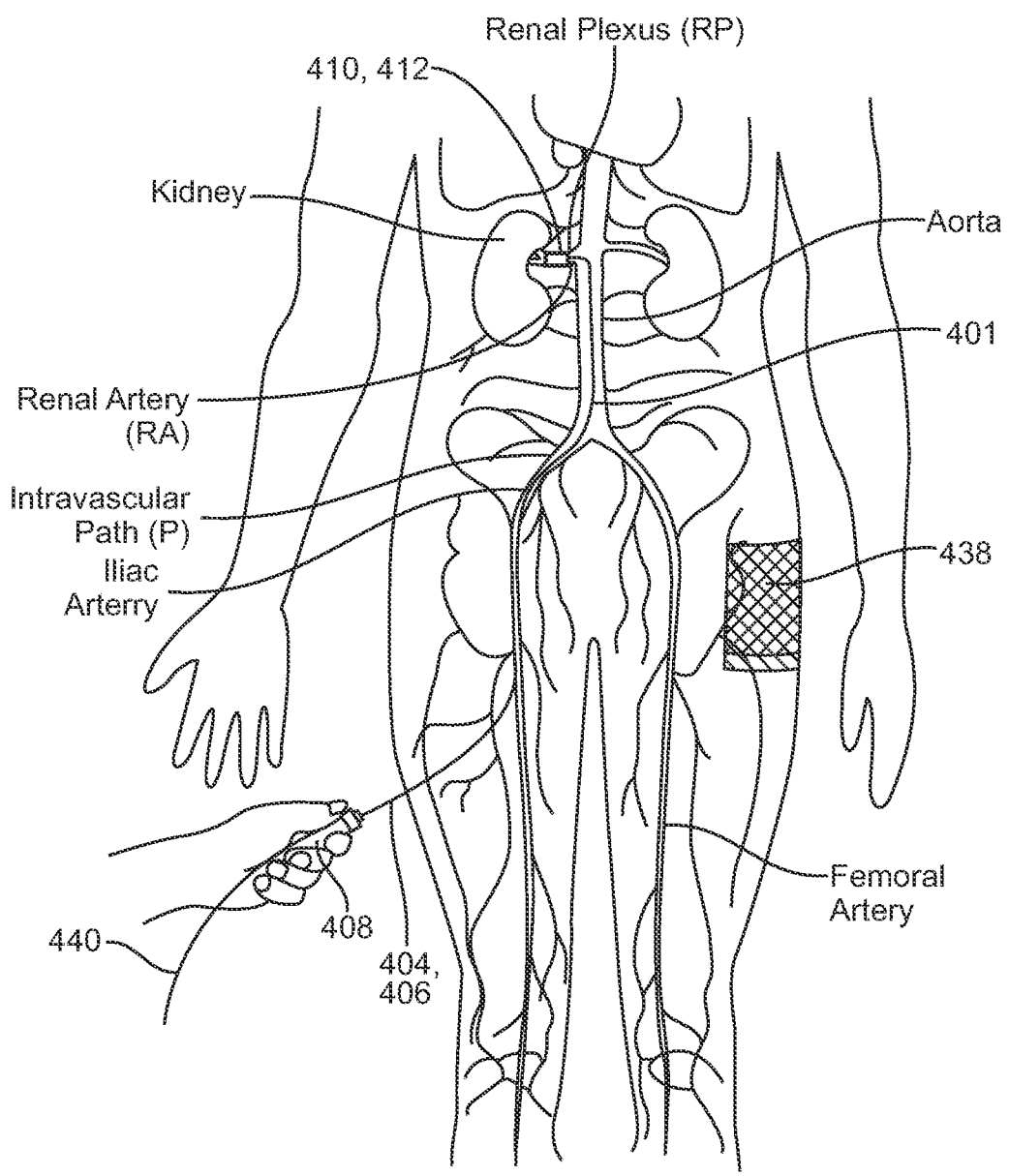
FIG. 5 illustrates modulating renal nerves with a catheter apparatus configured in accordance with an embodiment of the present technology.

FIG. 5 (with additional reference to FIG. 4) illustrates modulating renal nerves with an embodiment of the system 400. The catheter 401 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 406 of the shaft 404 is exposed externally of the patient. By manipulating the proximal portion 406 of the shaft 404 from outside the intravascular path P, the clinician may advance the shaft 404 through the sometimes tortuous intravascular path P and remotely manipulate the distal portion 410 of the shaft 404. In the embodiment illustrated in FIG. 5, the therapeutic assembly 412 is delivered intravascularly to the treatment site using a guide wire 440 in an OTW technique. As noted previously, the distal end of the therapeutic assembly 412 may define a lumen or passageway for receiving the guide wire 440 for delivery of the catheter 401 using either OTW or RX techniques. At the treatment site, the guide wire 401 can be at least partially axially withdrawn or removed, and the therapeutic assembly 412 can transform or otherwise be moved to a deployed arrangement for delivering energy at the treatment site as described above with respect to FIGS. 1A-3. The guide wire 440 may comprise any suitable medical guide wire sized to slideably fit within the lumen. In one particular embodiment, for example, the guide wire 440 may have a diameter of 0.356 mm (0.014 inch). In other embodiments, the therapeutic assembly 412 may be delivered to the treatment site within a guide sheath (not shown) with or without using the guide wire 440. When the therapeutic assembly 412 is at the target site, the guide sheath may be at least partially withdrawn or retracted and the therapeutic assembly 412 can be transformed into the deployed arrangement. In still other embodiments, the shaft 404 may be steerable itself such that the therapeutic assembly 412 may be delivered to the treatment site without the aid of the guide wire 440 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the therapeutic assembly 412. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the catheter 401. Further, in some embodiments, image guidance components (e.g., IVUS, OCT) may be integrated with the catheter 401 and/or run in parallel with the catheter 401 to provide image guidance during positioning of the therapeutic assembly 412. For example, image guidance components (e.g., IVUS or OCT) can be coupled to at least one of the therapeutic assembly 412 to provide three-dimensional images of the vasculature proximate the target site to facilitate positioning or deploying the therapeutic assembly 412 within the target renal blood vessel.

Referring to FIGS. 4 and 5 together, the purposeful application of energy from the energy delivery portions 418 (e.g., the exposed regions of the energy delivering thermocouple wire) may be applied to target tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery portions 418 (FIG. 4) and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

In operation (and with reference to FIGS. 1A-5), after being positioned at a desired location within the renal artery RA of the patient, the therapeutic assembly 412 may be transformed from its delivery state (e.g., delivery state 101 shown in FIG. 1B) to its deployed state (e.g., deployed state 103 shown in FIG. 1C). The transformation may be initiated using an arrangement of device components as described herein with respect to the particular embodiments and their various modes of deployment. In one embodiment, for example, the therapeutic assembly 412 may be deployed by retracting the guide wire 440 until a distal tip of the guide wire 440 is generally aligned with the tip 420 of the catheter 401. In some embodiments, the guide wire 440 may have a varying stiffness or flexibility along its length so as to provide increased flexibility distally. When the varying flexible guide wire 440 is partially retracted as described above, the pre-set spiral shape of the control member 124 (FIG. 1A) provides a shape-recovery force sufficient to overcome the straightening force provided by the distalmost portion of the guide wire 440 such that the therapeutic assembly 412 can deploy into its spiral configuration. Further, because the flexible distal portion of the guide wire 440 remains within the therapeutic assembly 412 in the deployed state 101 (e.g., FIGS. 1B and 2C), the guide wire 440 can impart additional structural integrity to the spiral-shaped portion during treatment. This feature is expected to help mitigate or reduce problems associated with keeping the therapeutic assembly 412 in place during treatment (e.g., help with vasoconstriction).

In another embodiment, the guide wire 440 may have a stiffness profile that permits the distal portion of the guide wire 440 to remain extended from an opening (not shown) in the tip 420 while still permitting the therapeutic assembly 412 to transform to its deployed state (e.g., deployed state 103 shown in FIG. 1C). In still other embodiments, the guide wire 440 may be withdrawn completely from the therapeutic assembly 412 (e.g., a distalmost end portion of the guide wire 440 is proximal of the therapeutic assembly 412) to permit the transformation, while a distalmost portion of the guide wire 440 remains within the shaft 404. In yet another embodiment, the guide wire 440 may be withdrawn completely from the shaft 404. In any of the foregoing examples, the clinician can withdraw the guide wire 440 sufficiently to observe transformation of the therapeutic assembly 412 to the deployed configuration and/or until an X-ray image shows that the distal tip of the guide wire 440 is at a desired location relative to the therapeutic assembly 412 (e.g., generally aligned with the tip 420, completely withdrawn from the therapeutic assembly 412, etc.). In some embodiments, the extent of withdrawal for the guide wire 440 can be based, at least in part, on the clinician's judgment with respect to the selected guide wire and the extent of withdrawal necessary to achieve deployment.

After treatment, the therapeutic assembly 412 may be transformed back to the low-profile delivery configuration by axially advancing the guide wire 440 relative to the therapeutic assembly 412. In one embodiment, for example, the guide wire 440 may be advanced until the distal tip of the guide wire 440 is generally aligned with the tip 420, and the catheter 401 can then be pulled back over the stationary guide wire 440. In other embodiments, however, the distalmost portion of the guide wire 440 may be advanced to a different location relative to the therapeutic assembly 412 to achieve transformation of the therapeutic assembly 412 back to a low-profile arrangement.

Neuromodulation

Neuromodulation is the partial or complete incapacitation or other effective disruption of nerves innervating, for example, an organ. As an example, renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and in particular conditions associated with central sympathetic over-stimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves.

Various techniques can be used to partially or completely incapacitate neural pathways, such as those innervating the kidney. The purposeful application of energy (e.g., electrical energy, thermal energy) to tissue by energy delivery element (s) or components such as those described in conjunction with the catheter devices above, can induce one or more desired thermal heating effects on localized regions of the renal artery and adjacent regions of the renal plexus, which lay intimately within or adjacent to the adventitia of the renal artery. The purposeful application of the thermal heating effects can achieve neuromodulation along all or a portion of the renal plexus.

The thermal heating effects can include both thermal ablation and non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity (RSNA) is expected.

Further Examples

The following examples are illustrative of several embodiments of the present technology:

1. A method of manufacturing a medical device for neuromodulation (e.g., neuromodulation of renal nerves), the method comprising:
   positioning a thermocouple assembly along a distal portion of a catheter, wherein the thermocouple assembly comprises a first wire and a second wire composed of dissimilar metals, and wherein the thermocouple assembly comprises a thermocouple junction at least proximate the distal portion;
   wherein the first wire has a plurality of exposed and insulated regions along a portion of the first wire proximate the distal portion, and the second wire of the thermocouple assembly remains insulated; and
   wherein the distal portion of the catheter includes an elongated tubular shaft configured to transform between a delivery configuration and a deployed configuration at a target treatment site within a blood vessel of a human patient, and wherein, in the deployed configuration, the exposed regions of the first wire define a plurality of energy delivery portions positioned to deliver electrical energy (e.g., RF energy, pulsed energy) to target tissue adjacent a wall of the blood vessel.
2. The method of example 1 wherein disposing a thermocouple assembly along a distal portion of a catheter comprises helically positioning the thermocouple assembly about the shaft.
3. The method of example 1 or example 2 wherein the shaft comprises a tubular structure having a lumen therethrough and a self-expanding, shape-memory material disposed within the lumen.
4. The method of any one of examples 1-3 wherein the shaft comprises a tubular structure having a lumen therethrough and is composed of a Nitinol multifilar stranded wire.
5. The method of any one of examples 1-4 wherein the method further comprises coating the exposed regions of the first wire with a biocompatible conductive material.
6. The method of any one of examples 1-5 wherein the exposed regions along the first wire of the thermocouple assembly are in electrical communication with each other.
7. The method of any one of examples 1-6, further comprising selectively removing portions of the first wire of the thermocouple assembly to define a plurality of exposed and insulated regions.
8. The method of example 7 wherein selectively removing portions of the first wire of the thermocouple assembly comprises forming four exposed regions along the first wire.
9. The method of any one of examples 1-8 wherein, in the deployed configuration, the shaft carrying the thermocouple assembly comprises a radially expanded, generally spiral shape configured to contact the wall of the blood vessel and to allow blood to flow through the vessel.
10. The method of any one of examples 1-9, further comprising disposing one or more sleeves composed of insulative material about the thermocouple assembly and the shaft.
11. The method of example 10 wherein the sleeves comprise polyethylene terephthalate (PET) heat shrink tubing.
12. The method of any one of examples 1-11 wherein the first wire is composed of copper and the second wire is composed of constantan.
13. The method of any one of examples 1-11 wherein the first wire is composed of silver coated nickel and the second wire is composed of constantan.
14. The method of any one of examples 1-11 wherein the first wire is composed of nickel and the second wire is composed of constantan.
15. The method of any one of examples 1-11 wherein the first wire is composed of silver and the second wire is composed of constantan.
16. A catheter apparatus, comprising:
   an elongated tubular shaft in a distal portion of the catheter apparatus, the shaft having a pre-formed spiral shape; and
   a therapeutic assembly disposed at the distal portion of the catheter apparatus and adapted to be located at a target location within an artery (e.g., a renal artery) of a human patient, the therapeutic assembly comprising a thermocouple assembly helically wrapped about the shaft, wherein the thermocouple assembly comprises a thermocouple junction at least proximate a distal portion of the shaft, and a first wire and a second wire composed of dissimilar metals, wherein the first wire comprises a plurality of exposed and insulated regions along the shaft, and further wherein the second wire is insulated along the shaft,
   wherein the elongated tubular shaft and the therapeutic assembly together define therethrough a guide wire lumen configured to slideably receive a medical guide wire,
   wherein axial movement of the guide wire relative to the therapeutic assembly transforms the shaft between (a) a low-profile delivery configuration and (b) a deployed configuration tending to assume the pre-formed spiral shape of the shaft,
   wherein, in the deployed configuration, the exposed regions of the first wire define a plurality of energy delivery portions positioned to deliver electrical energy (e.g., RF energy, pulsed energy) to target tissue adjacent a wall of the artery.
17. The catheter apparatus of example 16 wherein, in the deployed configuration, the energy delivery portions of the first wire are spaced apart from each other along a longitudinal axis of the artery and are configured to maintain apposition with a wall of the artery.
18. The catheter apparatus of example 16 or example 17 wherein the shaft comprises a tubular member having a lumen therethrough and is composed of a Nitinol multifilar stranded wire.
19. The catheter apparatus of any one of examples 16-18 wherein the exposed regions along the first wire of the thermocouple assembly do not contact each other in the delivery or deployed configurations.

20. The catheter apparatus of any one of examples 16-19 wherein the individual energy delivery portions are in electrical communication with each other.
21. The catheter apparatus of any one of examples 16-20 wherein the first wire of the thermocouple assembly comprises four energy delivery portions.
22. The catheter apparatus of any one of examples 16-21 wherein the therapeutic assembly does not include any electrodes.
23. The catheter apparatus of any one of examples 16-22 wherein the energy delivery portions are configured to deliver a thermal radiofrequency field to target nerves adjacent the wall of the artery.
24. A catheter system, comprising:
    an electric field generator configured to deliver radiofrequency (RF) energy to target tissue of a human patient;
    a catheter having a distal portion configured for placement within a blood vessel of the patient;
    a treatment assembly at the distal portion of the catheter, wherein the treatment assembly is selectively transformable between a low-profile delivery configuration and a deployed configuration sized to fit within the blood vessel;
    a thermocouple arranged about the distal portion of the catheter and electrically connectable to the electric field generator, wherein the thermocouple comprises—
        a first conductive wire having a plurality of predefined uninsulated regions at the distal portion of the catheter that define RF energy delivery portions positioned to deliver RF energy to the target tissue when the treatment assembly is in the deployed configuration;
        a second insulated wire adjacent to the first wire and composed of a different material than the first wire; and
        a thermocouple junction at least proximate the distal portion of the catheter.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:
1. A system comprising:
    an elongated shaft configured to radially expand from a delivery configuration to a deployed configuration;
    an energy delivery wire separate from the elongated shaft and extending along at least a portion of the elongated shaft, the energy delivery wire including a plurality of exposed regions separated from each other by insulated regions, wherein the exposed regions define a plurality of energy delivery portions configured to deliver energy to tissue of a patient; and
    a plurality of temperature sensors proximate to or within the energy delivery portions.
2. The system of claim 1, wherein the energy delivery wire is helically wrapped about the shaft.
3. The system of claim 1, wherein the plurality of temperature sensors comprise at least one of a thermocouple or a thermistor.
4. The system of claim 1, wherein at least one temperature sensor of the plurality of temperature sensors is proximate an energy delivery portion of the plurality of energy delivery portions.
5. The system of claim 1, wherein at least one temperature sensor of the plurality of temperature sensors is within an energy delivery portion of the plurality of energy delivery portions.
6. The system of claim 1, further comprising at least one of an impedance sensor, a pressure sensor, an optical sensor, or a flow sensor proximate to or within the plurality of energy delivery portions.
7. The system of claim 1, wherein in the deployed configuration, the elongated shaft defines a spiral shape.
8. The system of claim 1, wherein in the deployed configuration, the elongated shaft defines at least one of a lasso shape or a J-shape.
9. The system of claim 1, wherein the elongated shaft defines a guidewire lumen configured to receive a guidewire, wherein axial movement of the guidewire relative to the elongated shaft transforms the elongated shaft between the delivery configuration and the deployed configuration.
10. The system of claim 1, further comprising a thermocouple assembly including the energy delivery wire and a second wire electrically insulated along the elongated shaft, the second wire being joined to the energy delivery wire at a junction.
11. The system of claim 10, wherein the energy delivery wire and the second wire are formed of dissimilar metals.
12. The system of claim 1, wherein further comprising at least one electrode separate from the energy delivery wire and configured to delivery energy to tissue of the patient.
13. The system of claim 1, further comprising a catheter including the elongated shaft and the energy delivery wire, wherein the catheter does not include any electrodes separate from the plurality of exposed regions.

14. The system of claim 1, further comprising a sleeve securing the energy delivery wire to the elongated shaft, wherein the sleeve comprises an electrically insulative material and defines at least one of the insulated regions.

15. The system of claim 1, wherein when the elongated shaft is deployed in the deployed configuration in an artery, energy delivery portions of the plurality of energy delivery portions are spaced apart from each other along a longitudinal axis of the artery and are configured to maintain apposition with a wall of the artery.

16. The system of claim 1, wherein the plurality of exposed regions do not contact each other in the delivery or deployed configurations of the elongated shaft.

17. The system of claim 1, wherein energy delivery portions of the plurality of energy delivery portions are in electrical communication with each other.

18. The system of claim 1, wherein the energy delivery wire defines 2 to 6 exposed regions.

19. The system of claim 1, wherein the elongated shaft comprises a tubular member defining a lumen and including a Nitinol multifilar stranded wire.

20. A system comprising:
a catheter comprising:
a shaft selectively transformable between a relatively low-profile delivery configuration and a spiral deployed configuration; and
an energy delivery wire wrapped about the shaft, the energy delivery wire including uninsulated regions separated from each other by electrically insulated regions, wherein the uninsulated regions are configured to deliver energy to target tissue of a patient; and
a plurality of temperature sensors proximate to or within the uninsulated regions of the energy delivery wire.

21. The system of claim 20, further comprising a sleeve extending around the shaft, wherein the sleeve comprises an electrically insulative material and defines at least one of the electrically insulated regions.

* * * * *